United States Patent [19]
Tu

[11] Patent Number: 6,161,548
[45] Date of Patent: Dec. 19, 2000

[54] ABLATION DEVICE AND METHODS THEREOF

[76] Inventor: Hosheng Tu, 2151 Palermo, Tustin, Calif. 92782

[21] Appl. No.: 09/317,397

[22] Filed: May 24, 1999

Related U.S. Application Data

[62] Division of application No. 08/982,792, Dec. 2, 1997, Pat. No. 5,938,658.

[51] Int. Cl.$^7$ ................................................ A61B 19/00

[52] U.S. Cl. .................................... 128/898; 606/41

[58] Field of Search ........................ 606/41, 42, 45–50; 607/101–105; 604/20–22; 128/898

[56] References Cited

U.S. PATENT DOCUMENTS

| | | | |
|---|---|---|---|
| 5,929,048 | 7/1999 | Falk et al. | 514/54 |
| 5,938,658 | 8/1999 | Tu | 606/41 |
| 5,948,009 | 9/1999 | Tu | 607/96 |
| 5,968,005 | 10/1999 | Tu | 604/20 |
| 5,997,534 | 12/1999 | Tu et al. | 606/41 |

*Primary Examiner*—Michael Peffley

[57] ABSTRACT

A medical ablation device and methods for treating canker sores wherein a flexible RF electrode comprising a fluid delivery capability is inserted into the mouth; the RF electrode being placed against and/or surrounding the canker sore region; RF energy being applied for a predetermined time and under a controlled temperature to the canker sore tissue through the electrode to cause internal lesions; and therapeutic agent being delivered to heal and/or soothe the tissues thereafter.

7 Claims, 7 Drawing Sheets

ABLATION DEVICE AND METHODS THEREOF

CROSS-REFERENCE TO RELATED APPLICATIONS

This is a division of application Ser. No. 08/982,792, filed on Dec. 2, 1997, now U.S. Pat. No. 5,938,658.

TECHNICAL FIELD OF THE INVENTION

The present invention generally relates to improved medical devices system and methods for medical purposes of creating lesions; and, more particularly, to such devices and methods for heating and treating the canker sores in a patient with controlled time and temperature, followed by delivering therapeutic agent to the lesion sites.

BACKGROUND OF THE INVENTION

Surgical procedures are usually used for treatment of cellular tissues requiring direct contact of target tissue with a medical instrument. Surgical procedures often lead to substantial trauma by exposing both the target and intervening tissue. Furthermore, precise placement of a treatment probe is difficult because of the location of a target tissue in the body or the proximity of the target tissue to easily damaged, critical body organs, nerves, or other components.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have advantage of using a destructive energy which is rapidly dissipated and reduced to a non-destructive level by conduction and convection to forces of circulating fluids and other natural processes.

Devices using microwave energy, radiofrequency energy, ultrasound energy, cryogenic, and laser energy, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna through a duct to the zone of treatment and apply energy diffusively through the duct wall into the surrounding tissue in all directions.

Canker sores are also known as aphthous ulcerations or recurrent aphthae, which are painful sores usually formed in the mucus membrane of the mouth. The sores first appear as small red lesions which quickly whiten and then break down to form shallow ulcers. Many people, especially the small children with less immunity to ulcerations, experience the pain and discomfort of canker sores for a period from several days up to a couple of weeks. While the cause of canker sores has not been identified, several pharmaceutical approaches have been taken. They only mask the sources of the problem for temporary relief of pain and stress.

Price, Jr. in U.S. Pat No. 5,686,095 entitled "Method of treating canker sores" teaches a method by which a fluoroquinolone is topically applied to the ulcerous area. Similarly, Alliger in U.S. Pat. No. 5,516,799 entitled "Method of treating small mouth ulcers" teaches a method of using a simple alpha hydroxy organic acid. Marcus et al. in U.S. Pat. No. 5,182,104 entitled "Topical virucidal composition for treatment of mucocutaneous tissue" teaches a method of topically applying composition with a virucidal impact on mucocutaneous tissue, inactivation of herpes virus and human papilloma virus as manifested in cold sore, canker sores, warts, fever blisters lesions, aptheous ulcerations. Leeds in U.S. Pat. No. 4,466,956 entitled "Method of therapy for oral herpes simplex" discloses serial application of povidone-iodine and then application of anti-inflammatory agent. Hodosh in U.S. Pat. No. 4,191,750 entitled "Method for treating canker sores" discloses a method of applying a nitrate of potassium, lithium, sodium, magnesium, calcium or strontium. However, none of said patents disclose the method for treating canker sores by radiofrequency (RF) ablation or other energy treatment.

Of particular interest to the present invention are RF therapeutic protocols which have proven to be highly effective as used by electrophysiologists for tachycardia treatment, by neurosurgeons for the treatment of Parkinson's disease, and for neurosurgeons and anesthetists for other RF procedures such as Gasserian ganglionectomy for trigeminal neuralgia and percutaneous cervical cordotomy for intractable pains. Radiofrequency ablation, which exposes a patient to minimal side effects and risks, is generally performed after locating the treatment sore sites. Radiofrequency energy, when coupled with a temperature control mechanism, can supply precise energy to the device-to-tissue contact site to obtain the desired temperature for the optimal effects.

Imran in U.S. Pat. No. 5,281,218 entitled "Catheter having needle electrode for radiofrequency ablation" teaches a needle electrode attached on a catheter for radiofrequency ablation. Though a needle-like electrode is beneficial to ablate a tissue point for deep lesion, it is not disclosed that said needle electrode is possible to make an area ablation to cover the entire canker sores region with a temperature control means for radiofrequency therapy and capability for delivering therapeutic agent.

Edwards et al. in U.S. Pat. No. 5,456,662 entitled "Method for reducing snoring by RF ablation of the uvula" teaches a medical ablation method for reducing snoring wherein a flexible RF electrode wire is inserted into an uvula and RF energy is applied to the uvula tissue to cause internal lesions. Edwards et al. does not disclose a catheter to ablate an area having capability for simultaneously delivering therapeutic agent.

While a radiofrequency procedure using an existing electrode device has had promising results, the device is exposed to the tissue contact point and the heat only covers a small region, resulting in inefficient treatment of canker sores. Therefore there is a need for a new and improved device system and methods using the more controllable radiofrequency current for generating the needed heat to treat the desired broad region of the canker sores. During RF energy is applied to an electrode means or immediately after applying RF energy, the therapeutic agent, such as anti-inflammatory agent or virucidal drug, is delivered to the lesion sites. By designing a device with temperature control means and substance delivery capability, the canker sores can be treated therapeutically.

SUMMARY OF THE INVENTION

In general, it is an object of the present invention to provide a method and an improved medical device for generating and controlling the heating to create lesions in the mucous membrane of the mouth. It is another object of the present invention to provide a method and a device for monitoring the temperature of the device and controlling the temperature through a closed-loop temperature control mechanism and/or algorithm. The location of the temperature sensor means is preferably at the proximity of the tip of the medical device. It is still another object of the invention to provide a method and a device for heating and treating the canker sores in a patient with controlled time and temperature, followed by delivering therapeutic agent to the lesion sites.

Briefly, heat is generated by applying radiofrequency energy to a hand-piece, which comprises electrode means, in contact with body tissue. A DIP type electrode which contacts the patient is connected to the Indifferent Electrode Connector on the RF generator. When using an alternating current outlet, the generator should be grounded to avoid electrical interference. Heat is controlled by the power of the RF energy delivered and the delivery duration. The standard RF energy generator means and its application through electrode means to a patient are well known for those who are skilled in the art.

It is one object of the present invention to deliver the RF energy to the electrodes of a hand-piece, the medical device. It is another object of the present invention to control the energy delivered at a specified temperature and time. It is another object of the present invention to deliver the energy to the tissue that contacts the conducting surfaces of the electrode means of the hand-piece. It is still another object of the invention not to deliver the energy to the tissue that surrounds the insulated surfaces of the hand-piece.

The method and apparatus of the present invention have several significant advantages over other known systems or techniques to treat the canker sores. In particular, the electrode means using controllable RF energy as a heat source in this invention, followed by delivering therapeutic agent to the lesion sites may result in a more efficient therapeutic effect which is highly desirable in its intended application on canker sores.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF EXEMPLARY EMBODIMENTS

Figure 1:
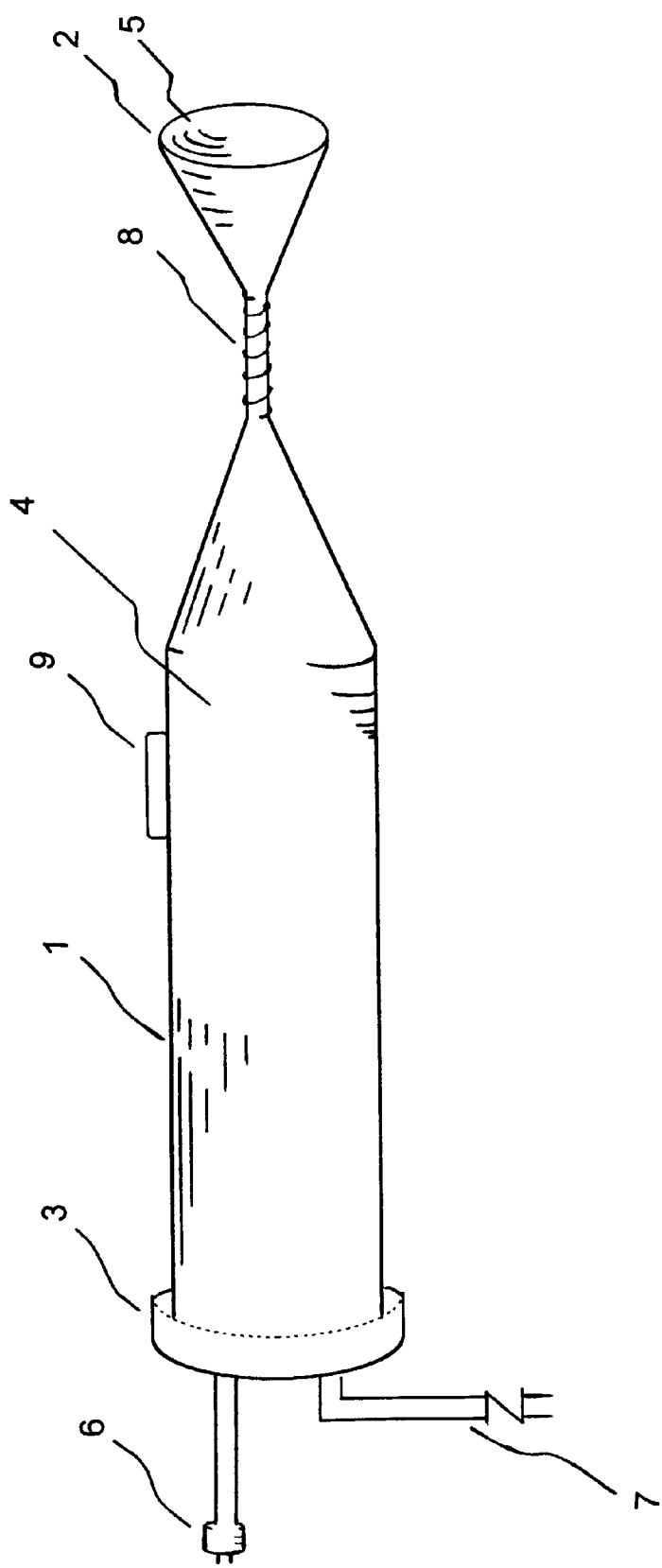
FIG. 1 is a perspective view of a hand-piece having electrode means and a fluid irrigation capability constructed in accordance with the principles of the present invention.

Referring to FIGS. 1 to 7, there is shown an embodiment of the ablation device system and a method of applying radiofrequency energy to treat the canker sores of a patient. As shown in FIG. 1, the device in the form of a hand-piece 1 comprises a distal end 2, a proximal end 3, and at least one lumen 4 therebetween; wherein electrode means 5 is disposed at said distal end 2, and wherein said electrode means has a plurality of surface zones for contacting the tissue. Said device system also comprises a connector 6 disposed at said proximal end 3 of the hand-piece 1; and means for applying radiofrequency energy to said electrode means 5 of the hand-piece. In another embodiment, a fluid infusion means 7 is provided for irrigation of desired therapeutic fluid to the canker sores site. The middle portion of the hand-piece comprises a coil-like element 8 so that the middle portion between the distal end and the proximal end is manually bendable or steerable. A RF energy switch button 9 is located at a convenient location on the hand-piece for a clinician to control the "on" and "off" action of RF energy delivery. The surface of said hand-piece, except the electrode means at its distal end, is not conductive.

Figure 2:
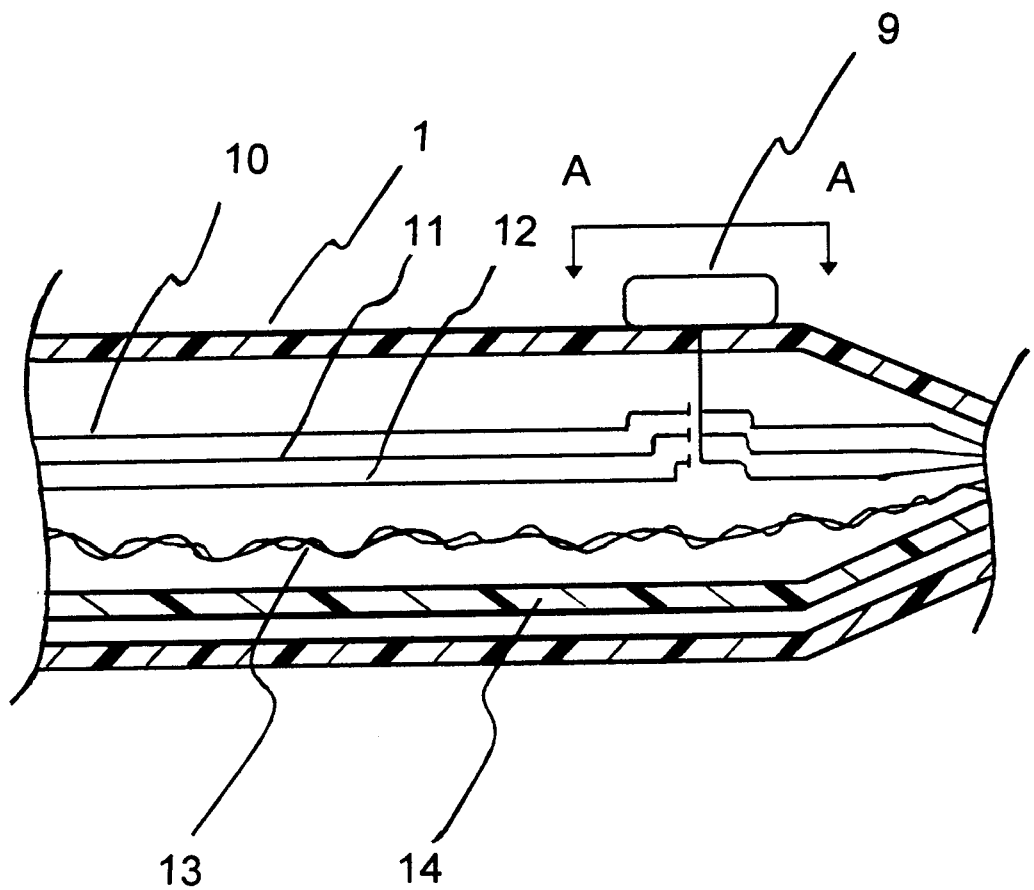
FIG. 2 is a cross-sectional view of the proximal portion of the hand-piece in FIG. 1.

FIG. 2 is a cross-sectional view of the proximal portion of the hand-piece 1. A plurality of RF energy conducting wires 10, 11, and 12 pass through the RF energy switch button 9 where each individual wire is controlled "on" and "off" by a clinician. One end of said conducting wire is secured to the electrode means 5 at the distal end of a hand-piece while the other end of the conducting wire is secured to a contact pin of the connector 6, from where said conducting wire is connected to an external RF generator (not shown).

A temperature sensing means 25 is secured to the electrode means. An insulated temperature sensor wire means 13 passes from the temperature sensing means at the distal end to an external temperature control mechanism through the outlet connector 6. The RF energy delivery is controlled by the temperature sensed and by a close-loop temperature control mechanism and/or algorithm. In one embodiment, a fluid infusion means is also provided for irrigation of the therapeutic agent. Said therapeutic agent is selected from the group of heparin, saline solution, fluoroquinolone, lactic acid, glycolic acid, alpha hydroxy organic acids, vitamins, povidone-iodine, nitrate compounds, virucidal agents, and antibiotics. A conduit 14 is provided inside the lumen for transporting said fluid from the proximal end of a hand-piece to the tissue contact site.

Figure 3:
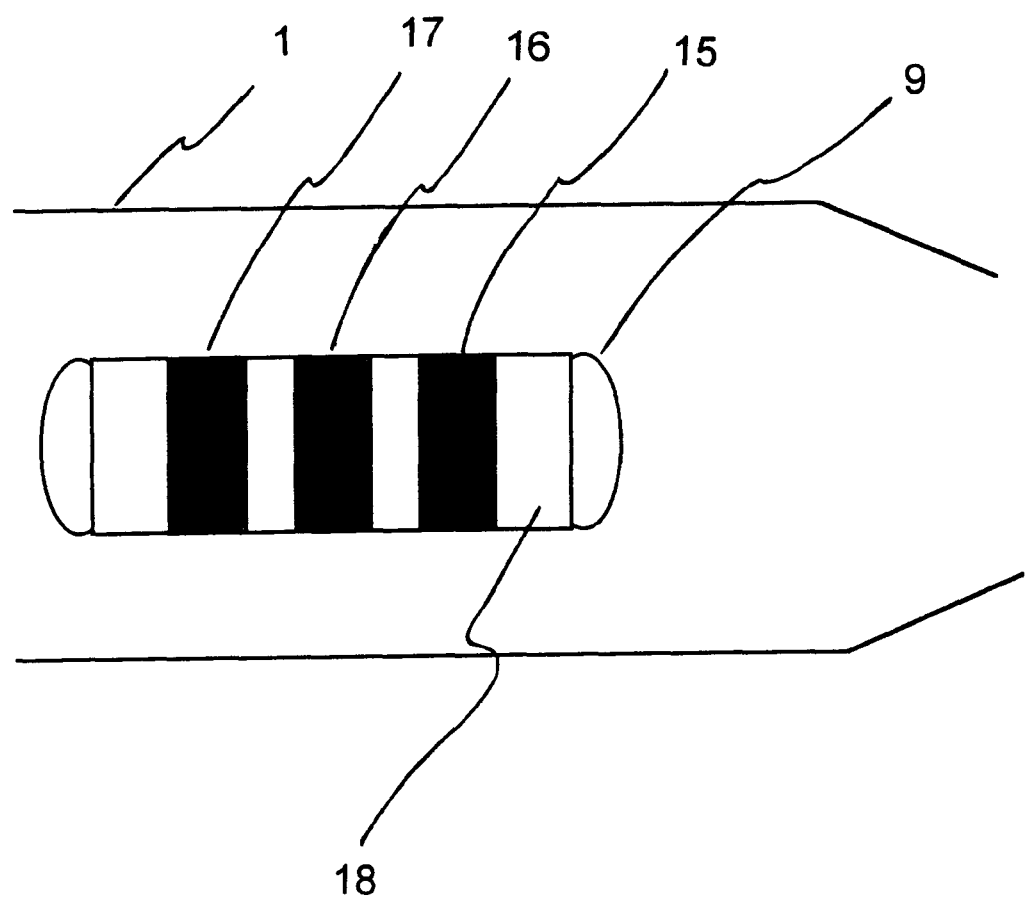
FIG. 3 is a top-view of the RF energy trigger button of FIG. 2

FIG. 3 is a top-view of the RF energy trigger button 9 of FIG. 2. It comprises at least one button or a plurality of buttons 15, 16, and/or 17, where each button controls one RF energy delivery means in a multiple RF delivery system. Each button can be individually controlled for selected RF energy delivery to a specific electrode. The base frame 18 of the trigger button 9 is secured to the outer surface of the hand-piece 1 at a convenient location for clinician's operation.

Figure 4:
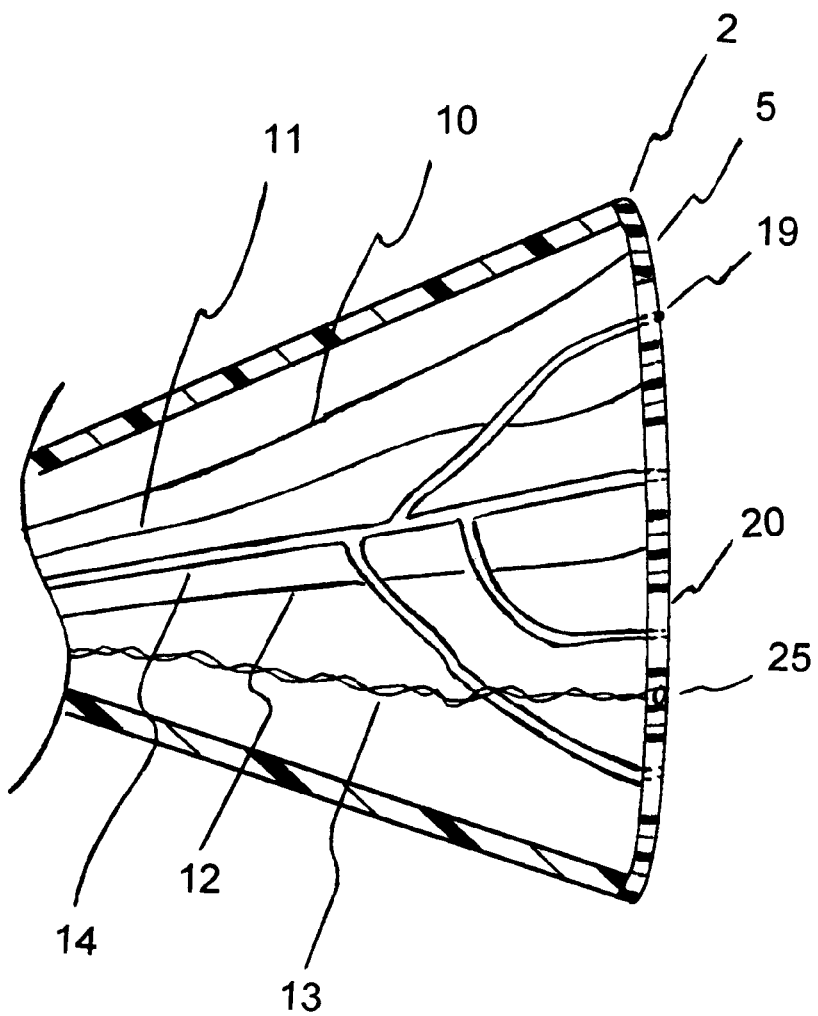
FIG. 4 is a cross-sectional view of the distal portion of the hand-piece in FIG. 1.

FIG. 4 is a cross-sectional view of the distal portion of the hand-piece 1. The electrode means 5 may include a coil-type electrode coil at the distal end 2 of a hand-piece, or may consist of a plurality of ring-type electrode rings. The fluid conduit 14 is to provide the therapeutic fluid to the irrigation port means 19 at the distal end 2 adjacent the electrode means 5.

Figure 5:
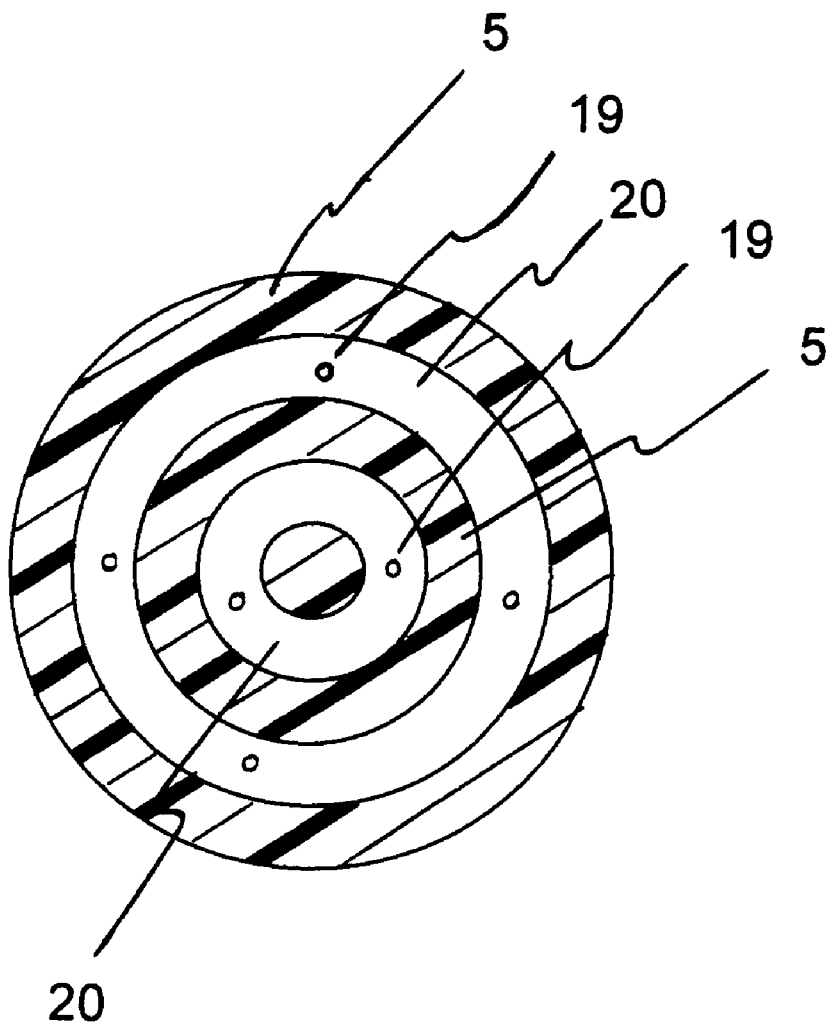
FIG. 5 is the end-view of the distal portion of the hand-piece.

FIG. 5 is an end-view of the distal portion of one type of the hand-pieces of the present invention. In this embodiment, a plurality of electrode rings constitutes the electrode means 5 of a hand-piece. Each electrode ring is connected with a conducting wire which passes through the trigger button 9 and terminates at the connector 6 at the proximal end 3 of a hand-piece. In a further embodiment, there is at least one non-conductive zone 20 between two electrode rings. At least one irrigation port 19 is disposed in the non-conductive zone 20. By simultaneously or sequentially applying RF energy to the electrode rings, the canker sores can be treated. Following the RF ablation, therapeutic fluid, in liquid or gel form, can be provided through the irrigation port 19 to the canker sores region.

Figure 6:
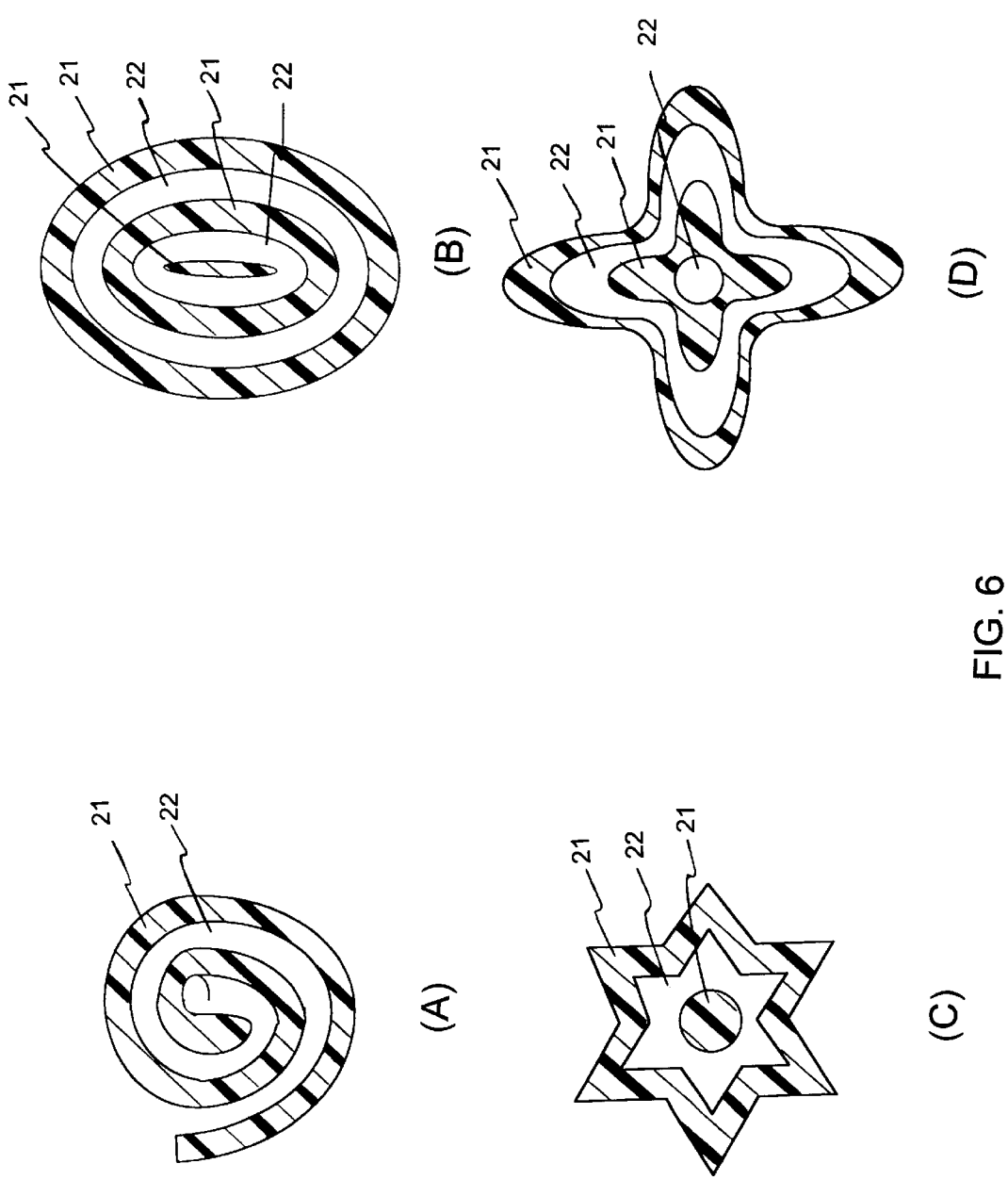
FIGS. 6A–6D show the end-view of the distal portion of the hand-piece for alternate devices design.

FIG. 6 shows the end-view of the distal portion of the hand-piece for alternate devices design. Various shapes of electrode means in the present invention are intended to cover different types of canker sores. The cross-sectional shape of the tip of said hand-piece can be a typical round shape (FIG. 5), whirlpool shape (FIG. 6A), oval shape (FIG. 6B), irregular shape, x-shape (FIG. 6D), and wheel-tooth shape (FIG. 6C) to increase the tissue contact efficiency and the canker sores treatment efficacy. The tip comprises at least one electrode means zone 21 and at least one non-conductive zone 22.

A method of applying radiofrequency energy to treat the canker sores of a patient comprises inserting a hand-piece into the mouth of a patient, wherein said hand-piece has a distal end, a proximal end, and at least one lumen therebetween, wherein electrode means is disposed at said distal end, and wherein said electrode means has a plurality of surface zones for contacting the tissue. The method also comprises contacting the canker sores of a patient with the electrode means of said hand-piece; applying radiofrequency energy to the electrode means of the hand-piece; and infusing and irrigating fluid to the canker sores region of a patient.

Figure 7:
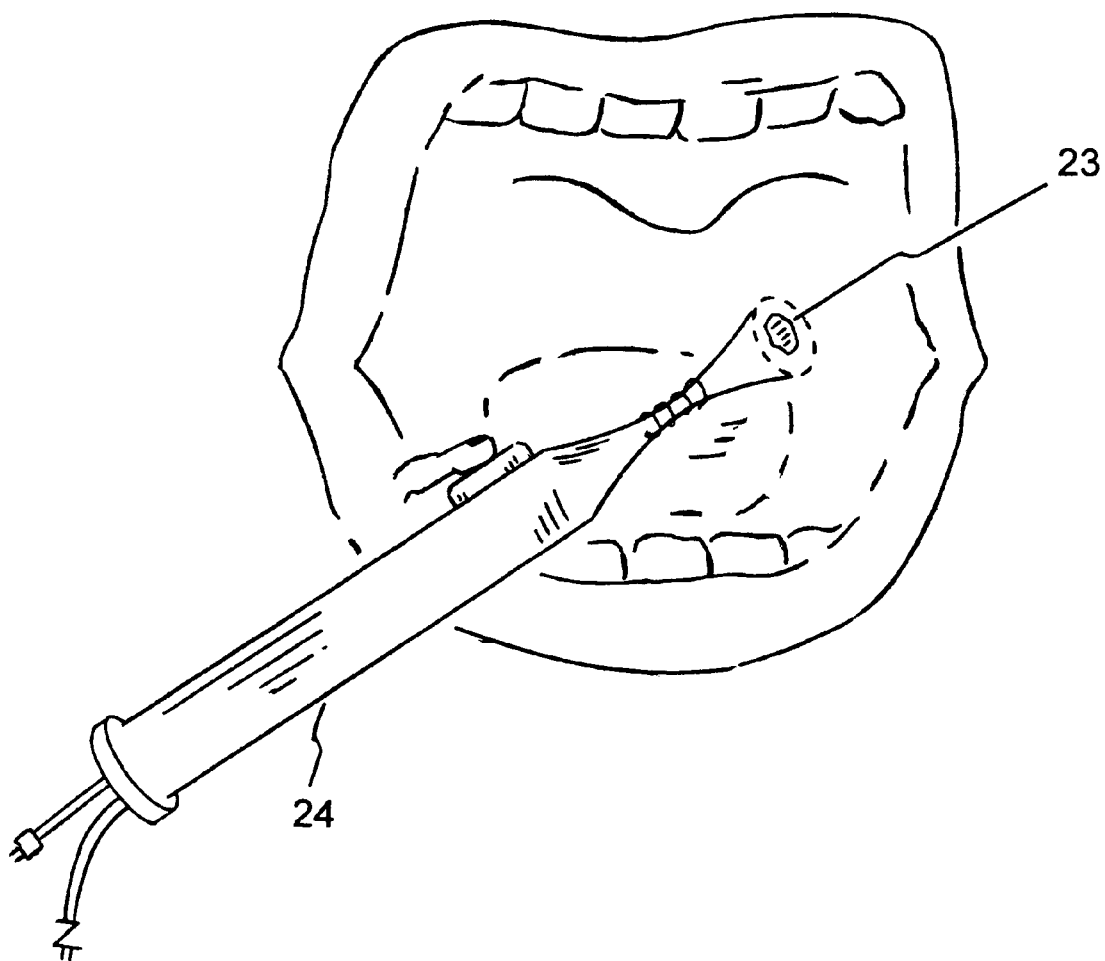
FIG. 7 shows a front view of a patient's mouth wherein the canker sores region is being ablated by the method of the present invention.

FIG. 7 shows a front view of a patient's mouth wherein a canker sores region 23 is being ablated by using the medical device 24 and methods of the present invention. The RF energy generator has the capability to supply RF energy by controlling the time, power and temperature, through a separate close-loop temperature control means. The patient is connected to the RF generator through a DIP electrode to form a close-loop current system. Therefore, radiofrequency energy is applied and delivered to the target canker sores region through the electrode means of this invention. The radiofrequency energy current in this invention is preferred within the range of 50 to 2,000 kHz.

In a particular embodiment, the area of the conducting surfaces of a hand-piece for canker sores treatment is from 5 mm$^2$ to 100 mm$^2$ or larger. The tissue contacting electrode means comprises at least one conducting surface zone. The material for the electrode means of this invention may consist of conductive metals such as platinum, iridium, gold, silver, stainless steel, Nitinol, or an alloy of these metals.

From the foregoing description, it should now be appreciated that a medical device system for canker sores comprising a RF generator and/or a fluid irrigation capability has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method of applying a radiofrequency energy to treat a canker sore of a patient, the method comprising:
   (a) inserting a hand-piece into a mouth of a patient, said hand-piece comprising a distal end, a proximal end, and at least one lumen extending therebetween, and a small diameter portion intermediate the proximal and distal ends, the small diameter portion being bendable to orient a distal face of the distal end; wherein electrode means is disposed on said distal face, said electrode means having a plurality of surface zones for contacting the tissue, wherein the hand-piece further comprises means for applying radiofrequency energy to the electrode means of the hand-piece and means for fluid infusion and irrigation capabilities;
   (b) contacting the canker sore with the electrode means;
   (c) applying radiofrequency energy to the electrode means; and
   (d) infusing and irrigating a fluid to the canker sore.

2. The method of applying a radiofrequency energy to treat a canker sore of a patient as in claim 1, further comprising a temperature sensor secured to the electrode means.

3. The method of applying a radiofrequency energy to treat a canker sore of a patient as in claim 2, further comprising means for controlling temperature of said temperature sensor by temperature controlling means.

4. The method of applying a radiofrequency energy to treat a canker sore of a patient as in claim 1, where the plurality of surface zones of said electrode means comprises at least one surface zone being non-conductive.

5. The method of applying a radiofrequency energy to treat a canker sore of a patient as in claim 1, further comprising a cross-sectional shape of a tip of said hand-piece being selected from the group consisting of a round shape, an oval shape, a x-shape, an irregular shape, and a wheel-tooth shape.

6. The method of applying a radiofrequency energy to treat a canker sore of a patient as in claim 1, wherein the fluid is selected from the group consisting of heparin, saline solution, fluoroquinolone, lactic acid, glycolic acid, alpha hydroxy organic acids, vitamins, povidone-iodine, nitrate compounds, virucidal agents, and antibiotics.

7. A method of applying a radiofrequency energy to treat a canker sore of a patient, the method comprising:
   (a) inserting a hand-piece into a mouth of a patient, said hand-piece comprising a distal end, a proximal end, and at least one lumen extending therebetween, and a small diameter portion intermediate the proximal and distal ends, the small diameter portion being bendable to orient a distal face of the distal end; wherein electrode means is disposed on said distal face, said electrode means having a plurality of surface zones for contacting the tissue, wherein the hand-piece further comprises means for applying radiofrequency energy to the electrode means of the hand-piece;
   (b) contacting the canker sore with the electrode means; and
   (c) applying radiofrequency energy to the electrode means.

* * * * *